(12) United States Patent
 Miura (10) Patent No.: US 8,777,450 B2
(45) Date of Patent: Jul. 15, 2014

(54) LIGHT IRRADIATION DEVICE

(75) Inventor: Kenji Miura, Uji (JP)

(73) Assignee: CCS, Inc., Kyoto (JP)

( * ) Notice: Subject to any disclaimer, the term of this patent is extended or adjusted under 35 U.S.C. 154(b) by 97 days.

(21) Appl. No.: 13/054,921

(22) PCT Filed: Jun. 1, 2009

(86) PCT No.: PCT/JP2009/059979
§ 371 (c)(1),
(2), (4) Date: Jan. 19, 2011

(87) PCT Pub. No.: WO2010/013540
PCT Pub. Date: Feb. 4, 2010

(65) Prior Publication Data
US 2011/0122623 A1 May 26, 2011

(30) Foreign Application Priority Data
Jul. 3, 2008 (JP) ................................. 2008-197040

(51) Int. Cl.
*F21S 4/00* (2006.01)
(52) U.S. Cl.
USPC ....................... 362/249.02; 257/99
(58) Field of Classification Search
USPC ........ 362/249.02, 252, 249, 800; 257/99–100
See application file for complete search history.

(56) References Cited

U.S. PATENT DOCUMENTS

| 2005/0073840 A1 | 4/2005 | Chou et al. |
| 2005/0207165 A1 | 9/2005 | Shimizu et al. |
| 2005/0242362 A1* | 11/2005 | Shimizu et al. ................. 257/99 |

FOREIGN PATENT DOCUMENTS

| CN | 1464953 | 12/2003 |
| CN | 201047560 | 4/2008 |
| JP | 11-162233 | 6/1999 |
| JP | 2006-275790 | 10/2006 |
| JP | 2007-507115 | 3/2007 |
| WO | 2005/034198 | 4/2005 |

OTHER PUBLICATIONS

Chinese Application No. 200980129991.0 Office Action dated Oct. 10, 2012, 7 pages with partial English translation (see chart on last page).

* cited by examiner

*Primary Examiner* — Anne Hines (57) ABSTRACT

The present invention uniforms a size of an LED substrate 2 to realize reduction of the number of parts and reduction of a manufacturing cost, and is a light irradiation device comprising: a long LED substrate 2 on which a plurality of same LEDs 21 are mounted; a chassis 3 having a substrate housing space for housing the LED substrate 2, wherein the number of LEDs 21 in which a difference between a power source voltage $V_E$ and a sum of a forward voltage $V_f$ in the series connection of the LEDs 21 is within an allowable range is employed as the number of LED units, and the number of LEDs 21 mounted on the LED substrate 2 is a common multiple of the number of LED units determined in each of LEDs 21 of different wavelengths.

20 Claims, 7 Drawing Sheets

LIGHT IRRADIATION DEVICE

TECHNICAL FIELD

The present invention relates to a light irradiation device that uses a plurality of LEDs and that is able to irradiate, for example, linear light, and especially relates to a light irradiation device that is preferably used for inspection of a work (a product); existence of a defect, reading of a mark, and so on in a predetermined irradiation area.

BACKGROUND ART

As shown in Patent literature 1, a light irradiation device such as a linear light irradiation device includes: a long LED substrate on which a plurality of LEDs are mounted; and a chassis for housing the LED substrate.

In the light irradiation device, the number of LEDs mounted on the LED substrate, the number of series-connected LEDs is restricted depending on relation between a power source voltage $V_E$ and a forward voltage $V_f$ of the LED.

For example, in a case where the power source voltage $V_E$ is 24V, the forward voltage $V_f$ of a red LED is approximately 2.2V, and the number of the red LEDs mounted on the LED substrate is 10. In addition, the forward voltage $V_f$ is approximately 3.3V in a case of a white LED, the number of the white LEDs mounted on the LED substrate is 6. Moreover, the forward voltage Vf of an infrared LED is approximately 1.5V, the number of the infrared LEDs mounted on the LED substrate is 15.

However, since the number of the LEDs mounted on the LED substrate varies as described above, a size of the LED substrate varies; accordingly it is required to prepare a dedicated LED substrate for each type of the LED. In addition, the chassis for housing the LED substrate also varies depending on the type of the LED, and accordingly there is a problem that requires the respectively suitable substrates.

CITATION LIST

Patent Literature

Patent literature 1: JP2006-275790A

SUMMARY OF INVENTION

Technical Problem

Accordingly, the present invention is provided to solve the above-mentioned problems at once, and in a light irradiation device using various types of LEDs, intends as a main problem to realize reduction of the number of parts and reduction of a manufacturing cost due to sharing of the parts by uniforming a size of a LED substrate.

Solution to Problem

Specifically, a light irradiation device according to the present invention includes: an LED substrate on which a plurality of same LEDs are mounted; a chassis having a substrate housing space for housing the LED substrate, wherein the number of LEDs in which a difference between a power source voltage and a sum of forward voltage in the series connection of the LEDs is within an allowable range is employed as the number of LED units, and the number of LEDs mounted on the LED substrate is a common multiple of the number of LED units determined in each of the different types of LEDs.

In this device, when employing a common multiple of the number of LED units determined in each of different types of LEDs, the number of LEDs mounted on the LED substrate can be the same as the number of LEDs mounted on the LED substrate in the respective different types of LEDs, and thus the sizes of the respective LED substrates on which the different types of LEDs are mounted can be the same. Additionally, in a case of manufacturing the light irradiation device using the different types of LEDs, the same chassis can be used as chassis for housing the LED substrate. For this reason, in the manufacturing of the light irradiation device, parts such as the LED substrate and the chassis can be shared, the number of parts can be reduced, and a manufacturing cost can be reduced.

In order not only to uniform the size of the LED substrate but also to improve the general versatility by minimizing the size, it is preferable that the number of LEDs mounted on the LED substrate is the least common multiple of the number of LED units determined in each of the different types of LEDs.

When the LED mounted on the LED substrate is a surface-mounted type (chip type) LED, it is required to provide an optical lens in front of the LED. On this occasion, it is required to prepare a dedicated optical lens in accordance with the number of the LEDs mounted on the LED substrate. According to the present invention, in a case where the surface-mounted type LED is mounted on the LED substrate, when employing the common multiple of the number of LED units for the number thereof and making the number of LEDs mounted on the LED substrate same in the respective different types of LEDs, a common optical lens can be used, and accordingly the effect of the present invention can be further pronounced.

Advantageous Effects of Invention

As described above, according to the present invention, the number of parts and a manufacturing cost can be reduced by uniforming a size of a LED substrate.

DESCRIPTION OF EMBODIMENTS

Figure 3:
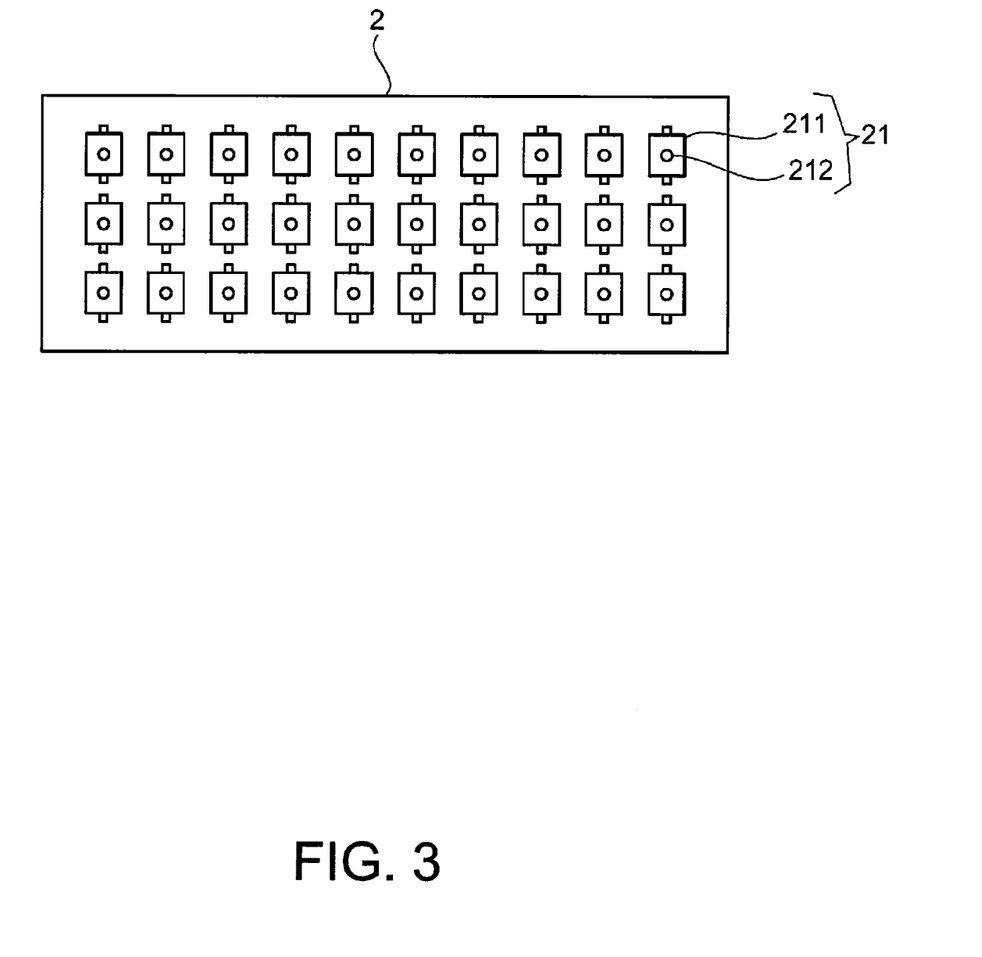
FIG. 3 is a plane view of a LED substrate on which LEDs are mounted
Figure 4:
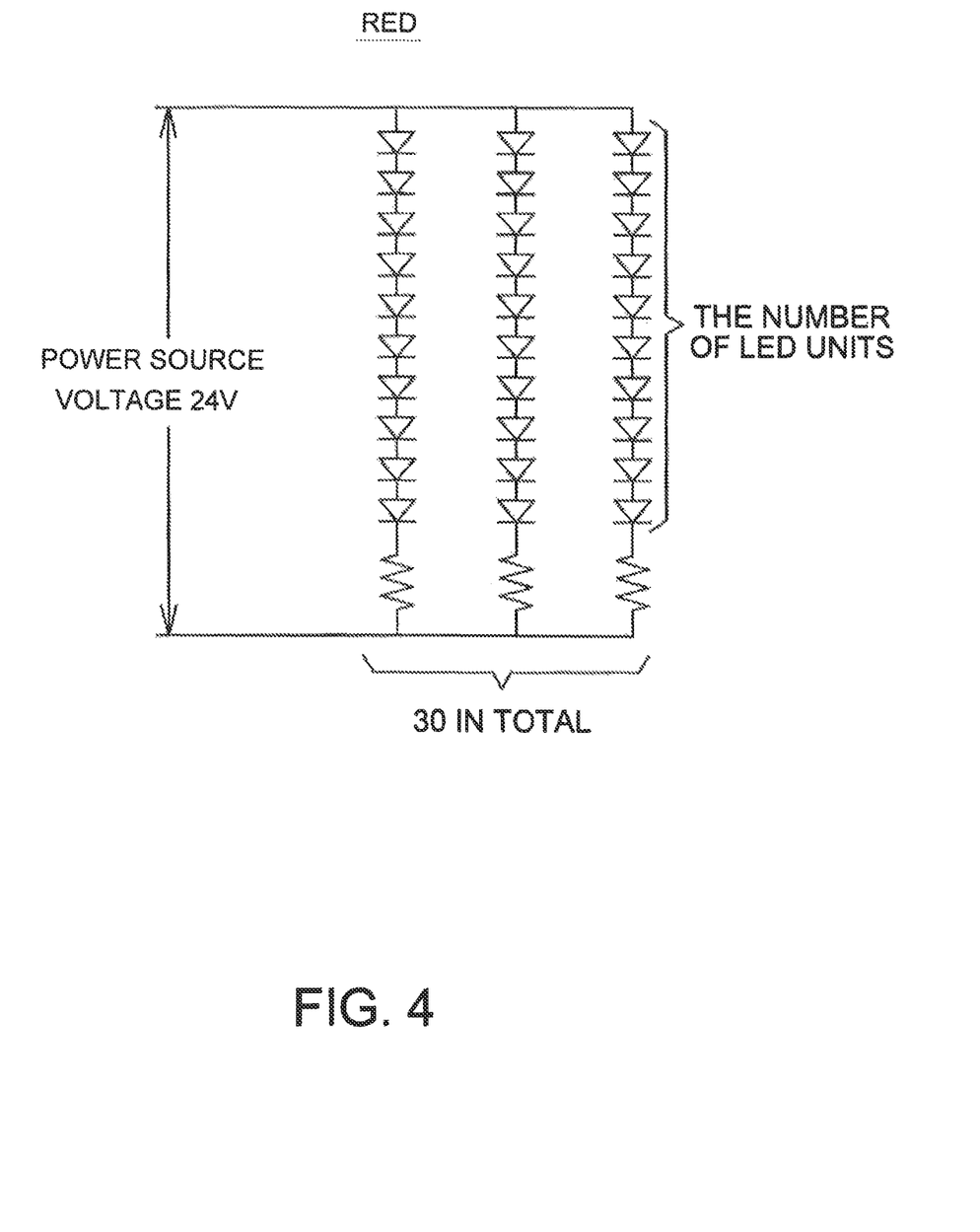
FIG. 4 is a circuit diagram of a case where red LEDs are mounted
Figure 5:
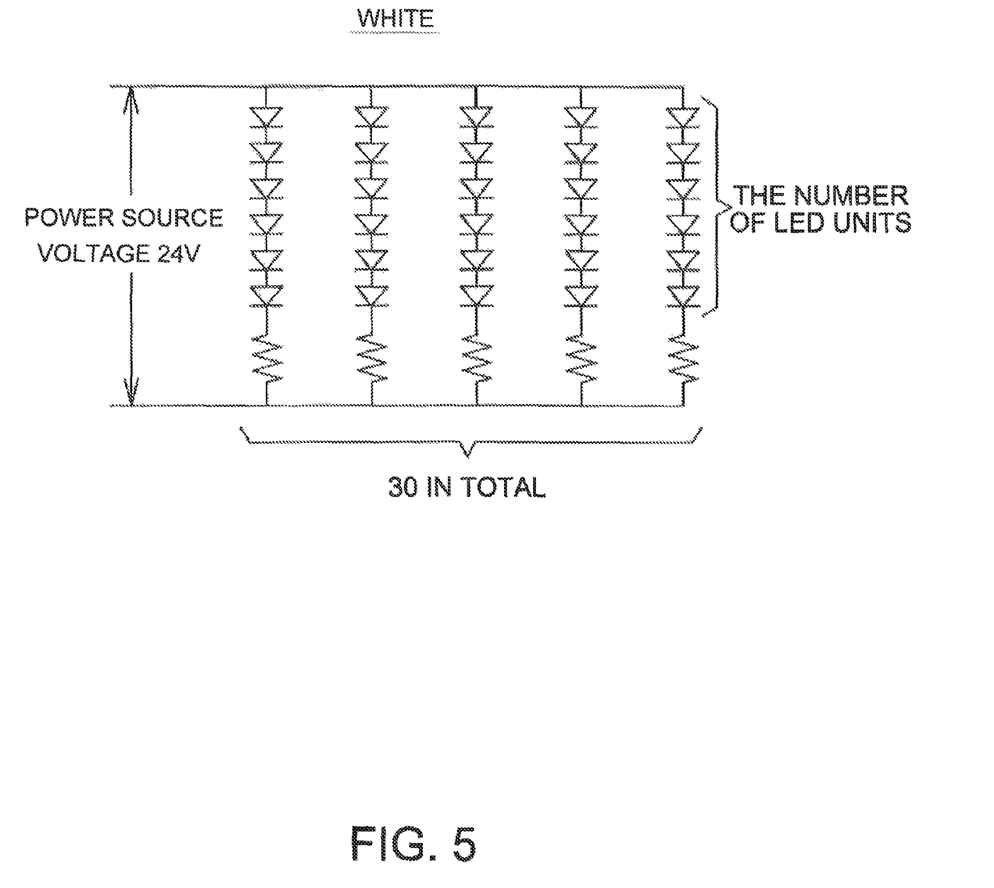
FIG. 5 is a circuit diagram of a case where white LEDs are mounted
Figure 6:
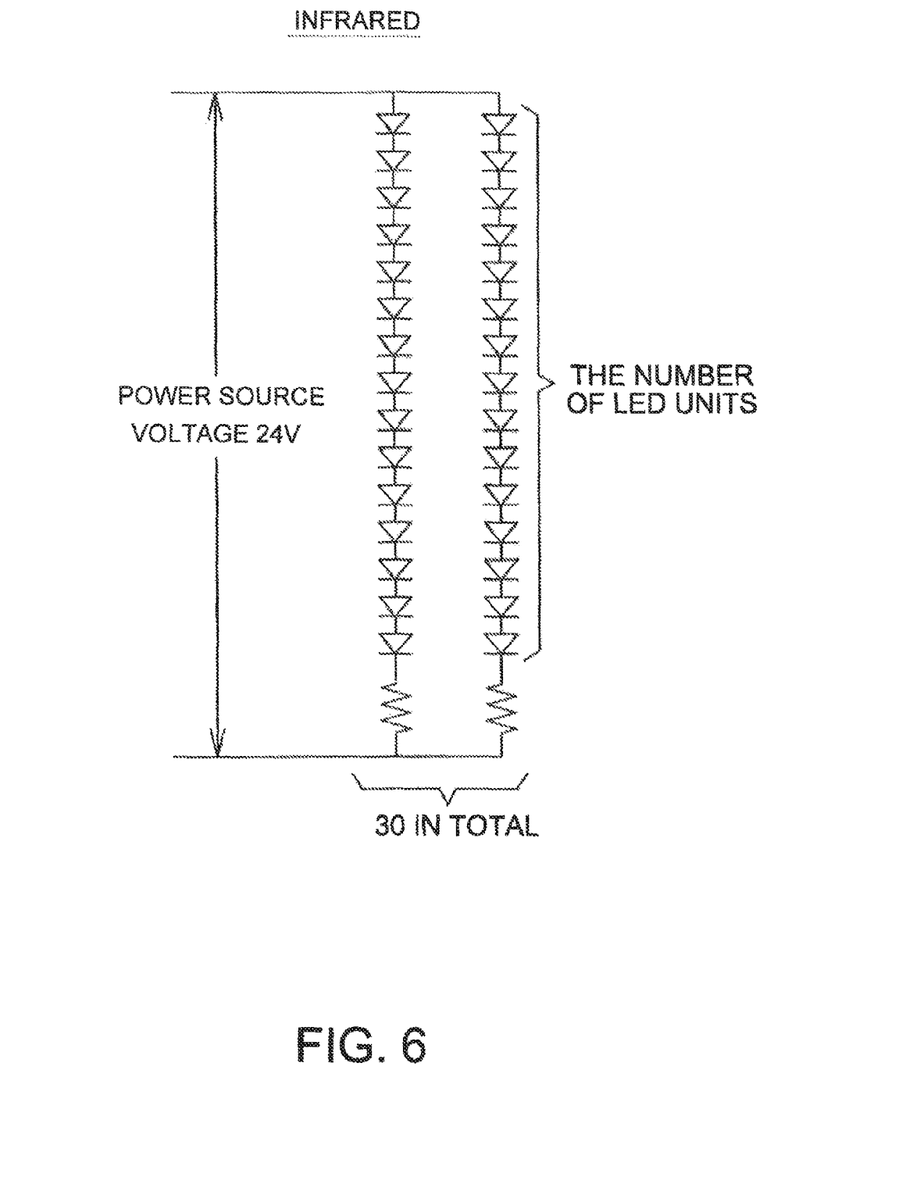
FIG. 6 is a circuit diagram of a case where infrared LEDs are mounted

Next, referring to drawings, one embodiment of a light irradiation device 1 according to the present invention will be explained. Meanwhile, FIG. 1 is a perspective view showing the light irradiation device 1 of the present embodiment, FIG. 2 is a cross section view of the light irradiation device 1, FIG. 3 is a plane view of an LED substrate 2 on which LEDs 21 are mounted, FIG. 4 is a circuit diagram of a case where the red LEDs 21 are mounted, FIG. 5 is a circuit diagram of a case where the white LEDs 21 are mounted, and FIG. 6 is a circuit diagram of a case where the infrared LEDs 21 are mounted.

<Device Configuration>

The light irradiation device 1 according to the present embodiment irradiates linear light, for example, to a predetermined irradiation area of an inspection object (a work), and is used for a product inspection system and the like for automatically inspecting a surface concerning existence of a defect and the like by imaging the predetermined irradiation area with an imaging device (not shown in the drawings) and by importing the obtained image data with an image processing device (not shown in the drawings).

Figure 1:
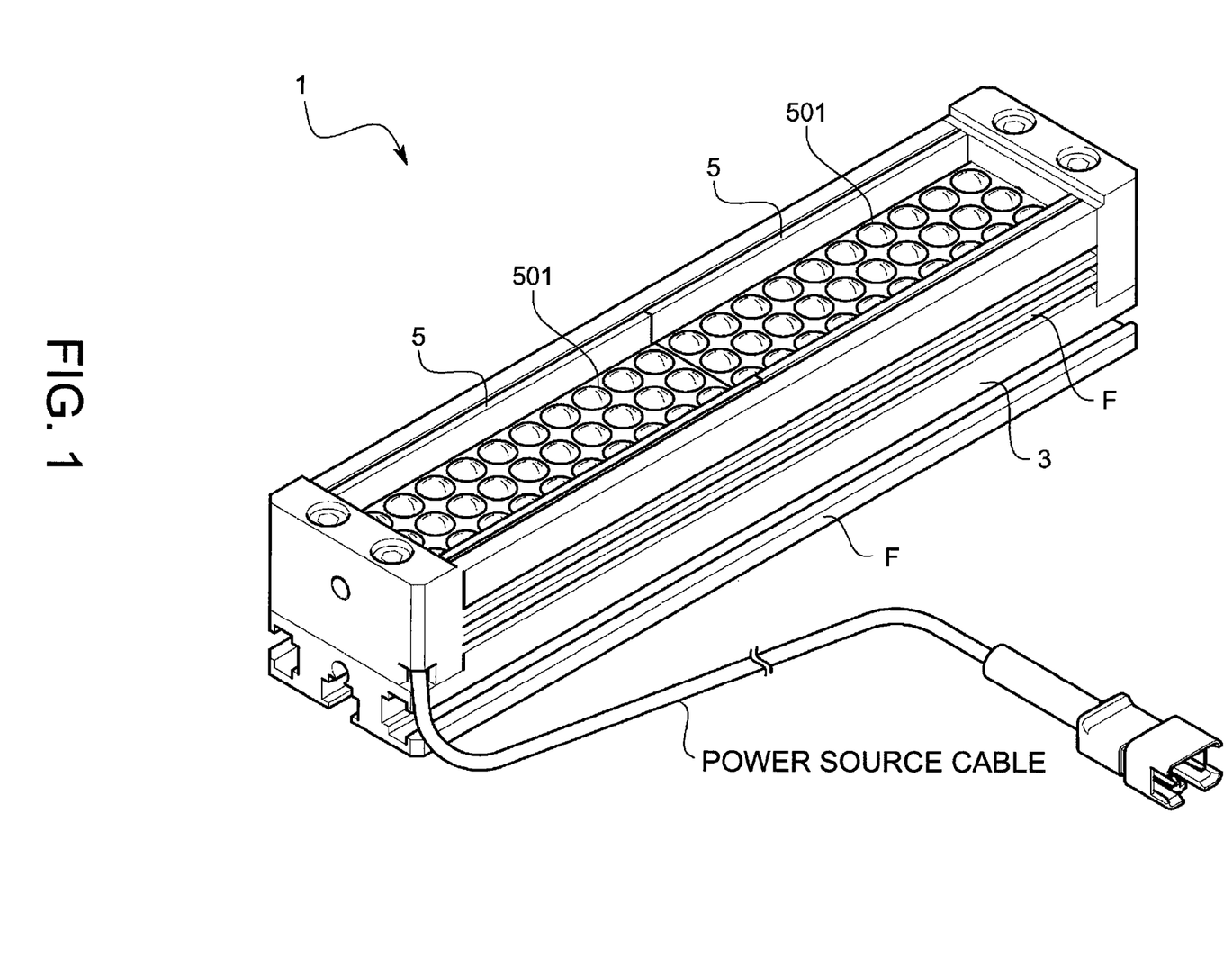
FIG. 1 is a perspective view of a light irradiation device according to the present invention
Figure 2:
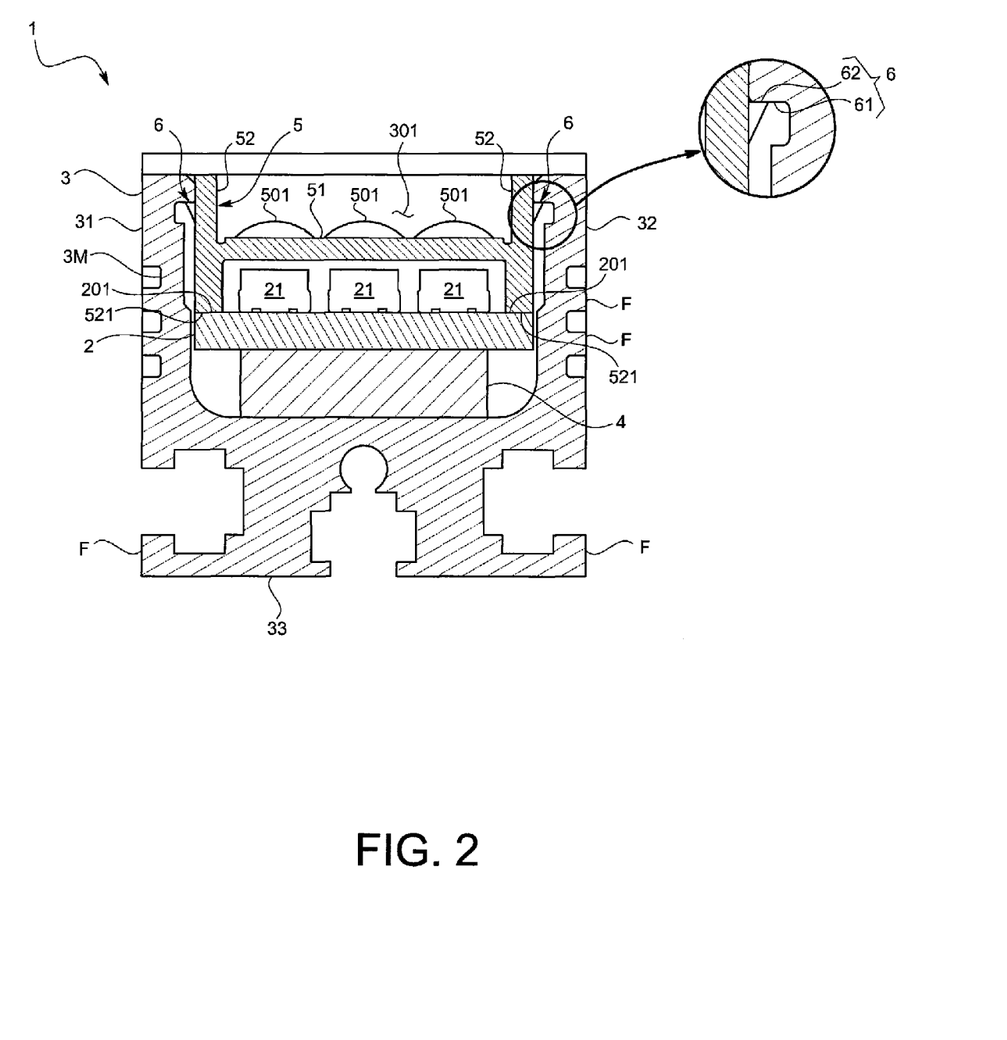
FIG. 2 is a cross section view according to an embodiment of the present invention

Specifically, as shown in FIGS. 1 and 2, the device includes: the LED substrate 2; a chassis 3; a heat transferring member 4; and a pressing member 5.

As shown in FIG. 3, the LED substrate 2 is a long substrate on which a plurality of the same LEDs 21 are mounted. Specifically, on the LED substrate 2, the plurality of LEDs 21 are mounted by machinery on a surface of a long printed-wiring substrate in one row or in plural rows in a short side direction (3 rows in the drawing) so that the optical axes can be arranged in an approximately one direction to be linear in the long side direction. To the LEDs 21, a voltage from a power source not shown in the drawing is controlled to be supplied by the voltage control circuit not shown in the drawing, and the LEDs are a surface-mounted type (a chip type) where LED elements 212 are arranged on a center of a package 211 having a thin rectangle plate shape for example. For example, the above-mentioned LEDs 21 are arranged so that the LED elements 212 can be arranged in line at a predetermined interval in both of the long side direction and the short side direction.

As shown in FIGS. 1 and 2, the chassis 3 has a housing concave portion 301 forming a substrate housing space for housing the LED substrate 2. Specifically, the chassis 3 is long and metallic and has an approximately C-shaped cross section perpendicular to a longitudinal direction (a stretching direction), and thus the housing concave portion 301 is formed by right and left side walls 31 and 32 and a bottom wall 33. Meanwhile, the housing concave portion 301 according to the present embodiment houses two LED substrates 2, continuing in the longitudinal direction. In addition, the chassis 3 is integrally molded by the extrusion or pultrusion, a plurality of grooves 3M stretching in the longitudinal direction are provided on circumference surfaces of the right and left side walls 31 and 32 and of a bottom wall 33, and protrusions formed between the grooves 3M serve as a heat radiating fins F. In addition, the heat transferring member 4 is provided between the housing concave portion 301 and the LED substrate 2, and transfers heat generated by the LED substrate 2 to the chassis 3.

The heat transferring member 4 is a strip-shaped flat plate having approximately the same width as or slightly smaller width than that of the LED substrate 2, and is formed of material having predetermined viscoelasticity and an insulation property such as silicon. And, when the LED substrate 2 is pressed, the heat transferring member 4 is deformed to dent by parts such as a resistance arranged on a reverse side of the LED substrate 2, and ideally contacts in a surface a reverse surface of the LED substrate 2 to play a role of increasing a heat conduction efficiency from the LED 21 to the bottom wall 33 of the chassis 3.

As shown in FIG. 2, the pressing member 5 has a plurality of lens parts 501 each corresponding to each of the plurality of LEDs 21, and presses a long-side end part 201 of the LED substrate 2 toward a bottom surface of the housing concave portion 301 of the chassis 3. Meanwhile, in the present embodiment, the pressing members 5 are provided by being continuously arranged in series so as to correspond to the respective LED substrate 2 (refer to FIG. 1).

Specifically, the pressing member 5, for example, has an approximately H-shaped cross section perpendicular to the longitudinal direction, includes: a lens forming part 51 in which a lens part 501 is formed; and a flange part 52 that is formed at both ends on the long side of the lens forming part 51 and that is perpendicular to the lens forming part. When the pressing member 5 is housed in the housing concave portion 301, the flange part 52 is arranged so as to face the right and left side walls 31 and 32 of the chassis 3. And, almost all surface of a lower end surface 521 of the flange part 52 contacts to the long side end part 201 of the LED substrate 2, specifically, to a surface outer and upper than the LED 21 in the LED substrate 2. In this manner, an approximately even force is applied to the long side end part 201 of the LED substrate 2, and the LED substrate 2 is prevented from warping in the longitudinal direction. Additionally, in a state where a lower end surface 521 of the flange part 52 contacts to the long side end part 201 of the LED substrate 2, the flange part 52 is provided so that approximately all light emitted from the LEDs 21 can pass through the lens part 501.

Then, as shown in a partially-enlarged view of FIG. 2, the pressing member 5 is fixed to the chassis 3 by a fixing mechanism 6 including: a first surface 61 that is provided to one of the chassis 3 and the pressing member 5 and that faces the bottom surface side of the housing concave portion 301; and a second surface 62 that is provided to the other one of the chassis 3 and the pressing member 5 and that faces an opening side of the housing concave portion 301 contacting to the first surface 61.

Additionally, in a state where the first surface 61 and second surface 62 of the fixing mechanism 6 are abutted, provided is a positioning mechanism for positioning central axes of the plurality of lens parts 501 and respective optical axes of the plurality of LEDs 21 so as to coincide by fitting a convex part (not shown in the drawing) provided to one of the LED substrate 2 and the pressing member 5 to a concave portion that is provided to the other one of the LED substrate 2 and the pressing member 5 and that is fitted to the convex part. By the positioning mechanism, the LEDs 21 and the lens parts 501 are positioned toward the long side direction and toward the short side direction.

Thus, the number of the LEDs 21 mounted on the LED substrate 2 according to the present embodiment is the least common multiple of the number of LED units determined in each different type of the LEDs 21. Meanwhile, different types of the LEDs 21 include not only the LED where a wavelength of light to be irradiated is different but also the LEDs where the number of the LED elements provided in the package 211 is different even if the wavelength of light to be irradiated is the same. In any case, it is desirable that the packages 211 of the different types of LEDs 21 have the same shape. In addition, a method for determining the number of the LEDs 21 mounted on the LED substrate 2 is effective only in a case of controlling the plurality of LEDs 21.

Here, "the number of LED units" means the number of the LEDs 21 in which a difference $(V_E - V_f \times N)$ between the power source voltage $V_E$ and the sum $(V_f \times N)$ of the forward voltages $V_f$ in the series connection of the LEDs 21 is within an allowable range, that is, the number of the LEDs 21 to be connected in series with respect to the power source voltage $V_E$.

The forward voltage $V_f$ in the present embodiment is a forward voltage of each of the packaged LEDs 21. In addition, "the predetermined allowable range" is determined depending on a condition where a desired irradiation area can be realized by one of or a plurality of the LED substrate 21 in a case of mounting the LEDs 21 on the LED substrate 21 in accordance with a common multiple of the number of LED units determined in each of the different types of LEDs 21 (more specifically, a condition to minimize the least common multiple of the number of LED units determined in each of the different types of LEDs 21) and on a condition to maximize the number of LED units in each of the different types of LEDs 21.

For example, in a case where the light irradiation device 1 is incorporated in a FA (Industrial Automatic Instrument), that is, in a case where the power source voltage $V_E$ is a direct current of 24V, a case of manufacturing three types of the light irradiation devices 1, the red LED 21, the white LED 21, and the infrared LED 21 will be explained.

The forward voltage $V_f$ of the red LED 21 is approximately 2.2V, and the number of the red LEDs 21 able to be connected in series with respect to the power source voltage $V_E$ is 10. That is, the number of LED units of the red LED 21 is 10.

In addition, the forward voltage $V_f$ of the white LED 21 is approximately 3.3V, and the number of the white LEDs 21 able to be connected in series with respect to the power source voltage $V_E$ is 6. That is, the number of LED units of the white LED 21 is 6. Meanwhile, the number of the white LEDs 21 able to be connected in series may be 7; however, the number is determined to be a value for minimizing the least common multiple in consideration of a relationship with the number of LED units of other types of the LEDs 21.

Moreover, the forward voltage $V_f$ of the infrared LED 21 is approximately 1.5V, and the number of the infrared LEDs 21 able to be connected in series with respect to the power source voltage $V_E$ is 15. That is, the number of LED units of the infrared LED 21 is 15.

Then, 30 that is the least common multiple of: the number of LED units of the red LED 21 (10); the number of LED units of the white LED 21 (6); and the number of LED units of the infrared LED 21 (15) is employed as the number of LEDs 21 mounted on the LED substrates 2 of the respective colors.

As a connection method of the respective LEDs 21 on a circuit, the LEDs 21 of the number corresponding to the number of LED units are connected in series, and the groups of series-connected LEDs are connected in parallel so as to be the least common multiple. That is, as shown in FIG. 4, in the case of the red LED 21, the group of the red LEDs is formed by connecting in series ten red LEDs 21, and the groups are connected in parallel so that the number of the red LEDs 21 can be 30 in total (that is, the groups of red LEDs are connected to be three rows). In addition, as shown in FIG. 5, in the case of the white LED 21, the group of the white LEDs is formed by connecting in series six white LEDs 21, and the groups are connected in parallel so that the number of the white LEDs 21 can be 30 in total (that is, the groups of white LEDs are connected to be five rows). Moreover, as shown in FIG. 6, in the case of the infrared LED 21, the group of the infrared LEDs is formed by connecting in series fifteen infrared LEDs 21, and the groups are connected in parallel so that the number of the infrared LEDs 21 can be 30 in total (that is, the groups of infrared LEDs are connected to be two rows).

An arrangement mode of the LEDs 21 on the LED substrate 2 is the same in the LED substrates 2 of the respective colors, as described above, and as shown in FIG. 3, the LEDs 21 are arranged in a plurality of rows (three rows in FIG. 3) as described above so that the optical axes can be arranged in an approximately one direction to be linear in the long side direction.

Effect of the Present Embodiment

In the light irradiation device 1 configured in this manner according to the present embodiment, since the number of LEDs 21 mounted on the LED substrate 2 is configured to be the same by employing the least common multiple of the number of LED units of the different types of LEDs 21 even when the types of LEDs 21 are different, the sizes of the respective LED substrates 2 on which the different types of LEDs 21 are mounted can be the same. In addition, in a case of manufacturing the light irradiating device 1 using the different types of LEDs 21, the same chassis 3 can be used for housing the LED substrate 2. Accordingly, in the manufacturing of the light irradiating device 1, parts such as the LED substrate 2 and the chassis 3 can be shared, the number of parts can be reduced, and the manufacturing cost can be reduced.

In addition, since not only the size of the LED substrates 2 are the same but also the numbers of LEDs are the same, positions of the LEDs 21 on the LED substrates 2 can be the same in the LEDs 21 of the respective colors; even in a case of providing a lens member (the pressing member 5 in the present embodiment) in front of the LED 21, the same lens member (the pressing member 5) can be used regardless of the types of LEDs 21; general versatility can be given the lens member (the pressing member 5); the number of parts can be reduced; and the manufacturing cost can be reduced.

Moreover, since the least common multiple of the number of LED units of the different types of LEDs 21 is employed for the number of LEDs 21 mounted on the LED substrate 2, the size of the LED substrates 2 can be minimized, and thereby improving the general versatility.

Other Modified Embodiments

Meanwhile, the present invention is not limited to the above-mentioned embodiment. In the following explanations, the same numerals will be given members corresponding to the above-described embodiment.

Figure 7:
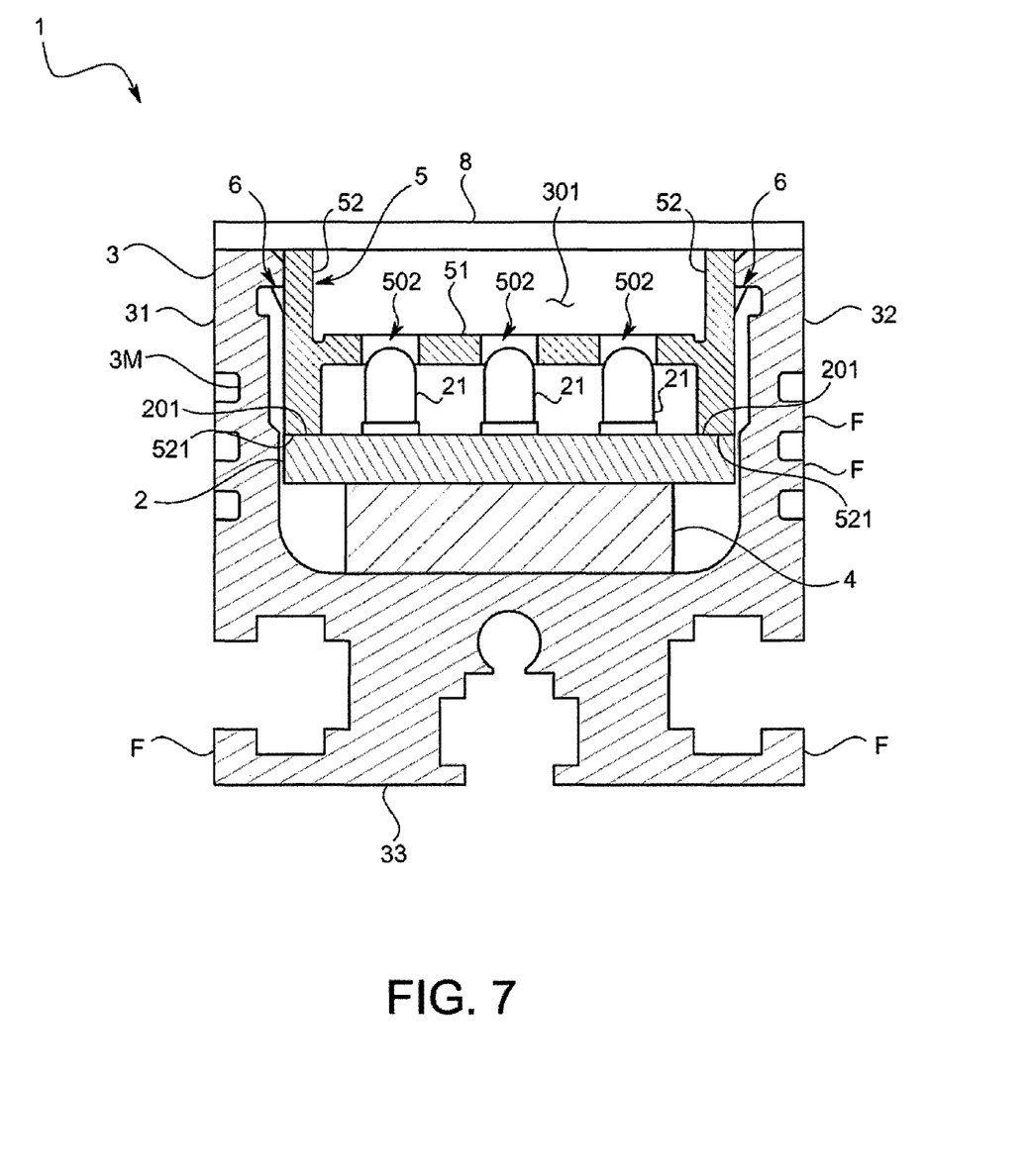
FIG. 7 is a cross section view of a light irradiation device according to another modified embodiment

For example, the pressing member 5 according to the embodiment includes the plurality of lens parts 501; however, as shown in FIG. 7, in a case where the LED 21 mounted on the LED substrate 2 is a bullet shape, the pressing member 5 may have though holes 502 provided corresponding to each of the plurality of LEDs 21. In this manner, a molding part 213 of the bullet-shaped LED 21 has a structure able to be inserted into the through hole 502, and light irradiated from the molding part 213 can be directly irradiated to the outside. Or, even in the case of the surface-mounted type LED 21, the light irradiated from the surface-mounted type LED 21 can be directly irradiated to the outside.

In addition, the light irradiation device 1 according to the embodiment may include a diffuser plate for diffusing the light from the LED 21 or an optical filter for selecting only a predetermined wavelength to make the wavelength transmissive.

Moreover, a length of the light irradiation device may be changed by corresponding the LED substrate to the pressing member and by changing the number of the LED substrate and pressing member to be connected in series.

Furthermore, when a plurality of pressing members having lens parts of different curvature factor are prepared and the pressing member fixed on the chassis is changed, the curvature factor of the lens part can be changed, and the light irradiation device having directionality suited to various purposes can be manufactured.

In addition, in the embodiment, the number of LEDs is the least common multiple; however, other common multiple may be employed.

Further additionally, the light irradiation device according to the embodiment has an approximately rectangular parallelepiped shape and the LED substrate has a long shape; however, the shapes are not limited to these shapes. For example, in a case where the light irradiation device has an approximately circular shape, the LED substrate may have a partially-circular shape.

In addition, the above-mentioned embodiment and a part of or all of modified embodiment may be combined arbitrarily, and it is needless to say that the present invention is not limited to the embodiment and may be variously modified within the scope of the invention.

INDUSTRIAL APPLICABILITY

By employing the present invention, the size of the LED substrate can be uniformed, and the number of parts and the manufacturing cost can be reduced.

REFERENCE SIGNS LIST

1 Light irradiation device
21 LED
2 LED substrate
301 Housing concave portion (Substrate housing space)
3 Chassis
$V_E$ Power source voltage
$V_f$ Forward voltage

The invention claimed is:

1. A light irradiation device comprising:
an LED substrate on which a plurality of a same type of LEDs are mounted;
a chassis having a substrate housing space for housing the LED substrate, wherein
for an LED type the number of LEDs in which a difference between a power source voltage and a sum of forward voltage in a series connection of the LEDs is within an allowable range is employed as a number of LED units for the LED type, and
the number of LEDs mounted on the LED substrate is a common multiple of the number of LED units determined in each LED type with different wavelengths or a different number of LED elements provided in an LED package.

2. The light irradiation device according to claim 1, wherein the total number of LEDs mounted on the LED substrate is a least common multiple of the number of LED units determined in each of the different types of LEDs.

3. The light irradiation device according to claim 1, wherein the LEDs are surface-mounted type of LED.

4. The light radiation device according to claim 1, wherein the chassis has an elongated C-shaped cross section perpendicular to a longitudinal direction and a pressing member has an approximately H-shaped cross section perpendicular to the longitudinal direction for connecting to the chassis to hold the LED substrate in the chassis.

5. The light irradiation device according to claim 4 wherein a heat transfer member is mounted in the chassis beneath the LED substrate and is held in place by a force from the pressing member applied directly to the LED substrate.

6. The light irradiation device according to claim 5 wherein the pressing member supports a plurality of lens parts for optical alignment with respective individual LEDs.

7. The light irradiation device according to claim 4 wherein the pressing member includes a fixing mechanism for extending under an overhanging surface of the chassis to lock and align the pressing member.

8. The light irradiation device according to claim 1 wherein:
the LED substrate on which the plurality of the same type of LEDs are mounted is a first LED substrate, and a plurality of only the same type of LEDs are mounted on the first LED substrate;
the substrate housing space is for housing the first LED substrate and a second LED substrate, the second LED substrate having a plurality of only a same type of LEDs mounted thereon with the LEDs on the second LED substrate being a different type of LEDs than the LEDs mounted on the first LED substrate;
the number of LEDs mounted on the first LED substrate is a common multiple of the number of LED units determined in the type of LEDs mounted on the first substrate and the number of LED units determined in the type of LEDs mounted on the second substrate.

9. The light irradiation device according to claim 8 wherein:
the number of LEDs mounted on the second LED substrate is a common multiple of the number of LED units determined in the type of LEDs mounted on the first substrate and the number of LED units determined in the type of LEDs mounted on the second substrate.

10. The light irradiation device according to claim 9 wherein:
the chassis is configured to house the first LED substrate and the second LED substrate simultaneously.

11. The light irradiation device according to claim 8 wherein the number of LEDs mounted on the first LED substrate is a least common multiple of the number of LED units determined in types of LEDs on substrates that the substrate housing space is configured to house.

12. The light irradiation device according to claim 8 wherein the number of LEDs mounted on the first LED substrate is a least common multiple of the number of LED units for each LED type mounted within the chassis.

13. A light irradiation device comprising:
a chassis having an LED substrate housing space;
a heat transferring member mounted on the chassis below the LED substrate housing space;
an LED substrate mounted on the heat transferring member in the LED substrate housing space, and having a plurality of LEDs mounted to irradiate light from the chassis, the plurality of LEDs include at least a first unit of LEDs of a first wavelength and a second unit of LEDs of a second wavelength different than the first wavelength, the number of LEDs in the first unit differ from the number of LEDs in the second unit, wherein the total number of the plurality of LEDs mounted in the chassis is a common multiple of the number of LEDs in the first unit and the number of LEDs in the second unit.

14. The light irradiation device according to claim 13 wherein the chassis has an elongated open cross section perpendicular to a longitudinal direction and a pressing member has a surface contacting the chassis to force the pressing member to contact and hold the LED substrate within the chassis.

15. The light irradiation device according to claim 14 wherein the pressing member includes a fixing mechanism for extending under an overhanging surface of the chassis to lock and align the pressing member.

16. The light radiation device according to claim 13, wherein the chassis has an elongated C-shaped cross section perpendicular to a longitudinal direction and a pressing member has an approximately H-shaped cross section perpendicular to the longitudinal direction for connecting to the chassis to hold the LED substrate in the chassis.

17. The light irradiation device according to claim 16 wherein the pressing member supports a plurality of lens parts for optical alignment with respective individual LEDs.

18. The light irradiation device according to claim 13 wherein the heat transferring member is mounted in the chassis beneath the LED substrate and is held in place by a force from a pressing member applied directly to the LED substrate.

19. A light irradiation device comprising:
an LED substrate on which a plurality of a first type of LEDs and a plurality of a second type of LEDs are mounted, the first type of LEDs providing different wavelengths and/or having a different number of LED elements provided in an LED package than the second type of LEDs;
a chassis having a substrate housing space for housing the LED substrate, wherein
for an LED type a number of LEDs in which a difference between a power source voltage and a sum of forward voltage in a series connection of the LEDs are within an allowable power range are employed as a number of LED units for the LED type; and
the total number of the first type and the second type of LEDs mounted on the LED substrate is a common multiple of the number of LED units determined in the first type of LEDs and in the second type of LEDs, with the number of the first type of LEDs mounted on the LED substrate being different than the number of the second type of LEDs mounted on the LED substrate.

20. The light irradiation device of claim 19, wherein the total number of LEDs mounted on the LED substrate is a least common multiple of the number of LED units mounted within the chassis.

* * * * *